United States Patent
Abe

(10) Patent No.: US 9,964,613 B2
(45) Date of Patent: May 8, 2018

(54) SHIMMING ASSISTANCE UNIT, SHIMMING ASSISTANCE METHOD, MRI APPARATUS AND MAGNET APPARATUS

(71) Applicant: Hitachi, Ltd., Tokyo (JP)

(72) Inventor: Mitsushi Abe, Tokyo (JP)

(73) Assignee: Hitachi, Ltd., Tokyo (JP)

(*) Notice: Subject to any disclaimer, the term of this patent is extended or adjusted under 35 U.S.C. 154(b) by 384 days.

(21) Appl. No.: 14/903,368

(22) PCT Filed: Jun. 24, 2014

(86) PCT No.: PCT/JP2014/066737
§ 371 (c)(1),
(2) Date: Jan. 7, 2016

(87) PCT Pub. No.: WO2015/005109
PCT Pub. Date: Jan. 15, 2015

(65) Prior Publication Data
US 2016/0146912 A1    May 26, 2016

(30) Foreign Application Priority Data
Jul. 9, 2013   (JP) ................... 2013-143669

(51) Int. Cl.
*G01V 3/00*       (2006.01)
*G01R 33/3873*    (2006.01)
(Continued)

(52) U.S. Cl.
CPC .......... *G01R 33/3873* (2013.01); *A61B 5/055* (2013.01); *G01R 33/5659* (2013.01); *G01R 33/3875* (2013.01); *H01F 7/202* (2013.01)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS 4,890,082 A   12/1989 Fujita
8,947,089 B2   2/2015 Abe et al.
(Continued)

FOREIGN PATENT DOCUMENTS

CN      101002678 A     7/2007
JP      2011-110065 A   6/2011
(Continued)

OTHER PUBLICATIONS

International Search Report of PCT/JP2014/066737.
Chinese Office Action received in corresponding Chinese Application No. 201480038679.1 dated Nov. 1, 2017.

*Primary Examiner* — Walter L Lindsay, Jr.
*Assistant Examiner* — Frederick Wenderoth
(74) *Attorney, Agent, or Firm* — Mattingly & Malur, PC

(57) ABSTRACT

The shimming work assistance unit performs singular value decomposition of a response matrix, which represents the relationship between an error magnetic field distribution and an adjusted magnetic moment placement distribution. From the multiple eigenmodes obtained, the eigenmodes are selected and added one by one in order from the eigenmode with the highest singular value, and the residual magnetic field error, which represents the fluctuation range of the difference between the magnetic field distribution, generated by the placement of the shimming magnetic moments corresponding to said eigenmode, and the error magnetic field distribution, is displayed on a display unit as a function graph of eigenmode order (line graph (1)).

8 Claims, 6 Drawing Sheets

(51) Int. Cl.
*A61B 5/055* (2006.01)
*G01R 33/565* (2006.01)
*H01F 7/20* (2006.01)
*G01R 33/3875* (2006.01)

(58) Field of Classification Search
USPC .......................................................... 324/307
See application file for complete search history.

(56) References Cited

U.S. PATENT DOCUMENTS

| | | |
|---|---|---|
| 2007/0164744 A1 | 7/2007 | Kuhara et al. |
| 2007/0241755 A1 | 10/2007 | Ikedo |
| 2011/0089943 A1 | 4/2011 | Abe et al. |
| 2012/0019247 A1* | 1/2012 | Boernert .............. G01R 33/288 |
| | | 324/309 |
| 2012/0268119 A1 | 10/2012 | Abe et al. |

FOREIGN PATENT DOCUMENTS

| | | |
|---|---|---|
| JP | 4902787 B | 3/2012 |
| JP | 2012-101105 A | 5/2012 |
| JP | 2013-059488 | 4/2013 |

\* cited by examiner

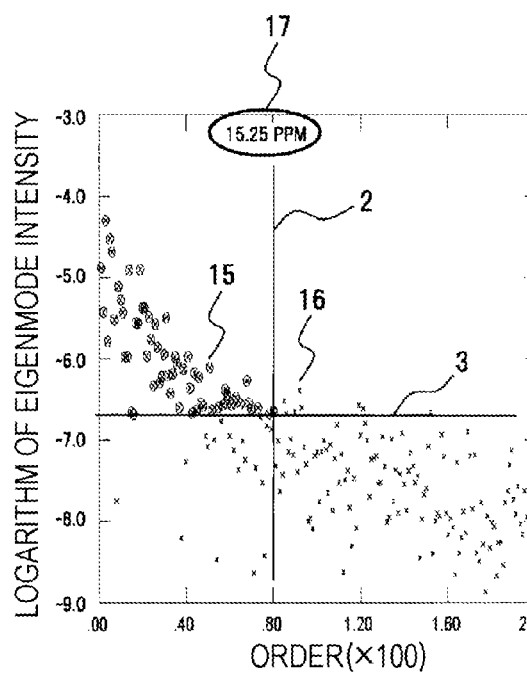 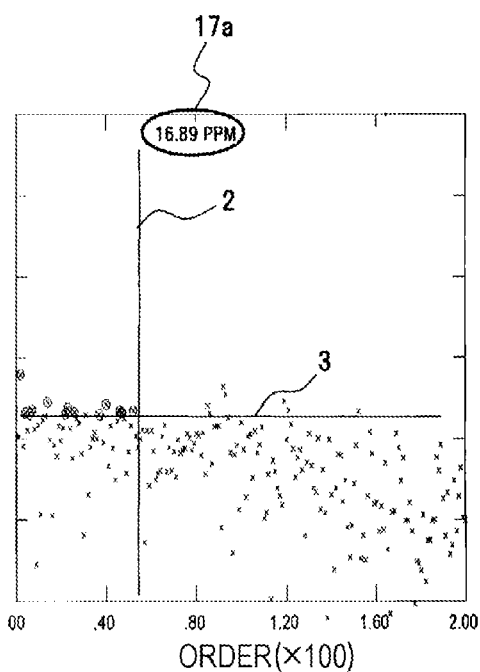
FIG. 6A — BEFORE SHIMMING HOMOGENEITY OF MAGNETIC FIELD DISTRIBUTION 726ppm
FIG. 6B — AFTER SHIMMING HOMOGENEITY OF MAGNETIC FIELD DISTRIBUTION 17ppm

SHIMMING ASSISTANCE UNIT, SHIMMING ASSISTANCE METHOD, MRI APPARATUS AND MAGNET APPARATUS

TECHNICAL FIELD

The present invention relates to a shimming assistance unit, a shimming assistance method for a magnet apparatus that needs precise magnetic field distribution adjustment, and a nuclear magnetic resonance tomographic imaging apparatus (hereinafter, referred to as magnetic resonance imaging (MRI) apparatus) that includes the shimming assistance unit.

BACKGROUND ART

An MRI apparatus uses a magnet of mainly a superconducting magnet. In some cases, however, it uses a permanent magnet and a normal conducting magnet. The magnet used in the MRI apparatus generates a static magnetic field requiring an accuracy which has a variation of about one millionth of a magnetic field intensity come to a problem.

The magnetic fields used in the MRI apparatus are broadly classified into the following three types.

(1) A magnetic field that is temporally and spatially constant and that normally has an intensity of 0.1 to several teslas or more, having the amount of variation within a space for performing imaging (space of a sphere or ellipsoid having diameter of 30 to 40 cm) of several ppm.

(2) A spatially gradient magnetic field and changes with a time constant of one second or less.

(3) A magnetic field generated by a high-frequency electromagnetic wave with a frequency (several MHz or more) that corresponds to nuclear magnetic resonance.

Among the three, the magnetic field (1) is required to be temporally constant and to have a highly accurate homogeneity spatially, in a space of area in which tomographic imaging is performed on a human body. Being highly accurate means having an accuracy with an order of one millionth, for example, ±1.5 ppm in an imaging space field of view (FOV) having a diameter of, for example, 40 cm. A magnetic field distribution which requires extremely highly accurate homogeneity is achieved by executing accurate adjustment of the magnetic field distribution after production and excitation of a magnet. A typical error magnetic field caused by a manufacturing error is 1000 times or more than a permissible error margin of the magnetic field demanded for a homogeneous magnetic field. This means that it is necessary to reduce an error magnetic field from several hundred ppm to several ppm in magnetic field adjustment (referred to as shimming) performed at a time of installation of a magnet after manufacturing of the magnet. Accordingly, the shimming requires an extremely high-level magnetic field adjustment technique.

Conventionally, this type of shimming uses a magnetic piece including an iron piece that is passively magnetized, a permanent magnet piece, a current loop, or the like, namely, something that has a magnetic moment (hereinafter, for simplification, referred to as a magnetic moment). In shimming, this magnetic moment is placed around a magnetic-field applied area. Adjusting an intensity and a placement position of the magnetic moment achieves a magnetic field distribution required for the magnetic-field applied area. In an MRI apparatus, the magnetic-field applied area means the imaging space FOV for diagnosis. Shimming is performed to achieve a magnetic field distribution with homogeneity within the space.

A typical magnetic moment for shimming is placed so as to cancel an error magnetic field distribution Ber. The error magnetic field distribution Ber is a vector having the amount of difference between a measurement magnetic field at each of magnetic field measurement positions and a target magnetic field distribution as an element. Herein, there are several hundreds of magnetic field measurement positions and there are several hundreds to tens of thousands or more of magnetic moment placement positions. With this placement, calculating placement of the magnetic moment for shimming would be a large-scale calculation.

Patent Literature 1, for example, describes as a calculation method for placing the magnetic moment, a truncated singular value decomposition (hereinafter, referred to as TSVD) method.

According to the TSVD method, a magnetic field distribution Bcom generated in a measured magnetic field area by a magnetic moment M placed for shimming is considered to be expressed as:

$$Bcom = A \cdot M \quad (1)$$

Based on the above, the magnetic moment M to be placed for shimming is determined such that the magnetic field distribution Bcom substantially corresponds to the error magnetic field distribution Ber.

Hereinafter in this description, the magnetic moment to be placed for shimming will be referred to simply as a shimming magnetic moment.

The shimming magnetic moment M is a vector having a magnetic moment magnitude at each of placement positions as an element. The number of elements may be several hundreds, several thousands or more. The magnetic field distribution Bcom is a vector having, as an element, the magnetic field intensity generated at each of magnetic field measurement points by the shimming magnetic moment M. A response matrix A is a matrix representing a relationship between the magnitude of the magnetic moment placed at each of the positions as the shimming magnetic moment M and the magnetic field intensity at each of the magnetic field measurement points. The response matrix A has an element of (number of magnetic field measurement points)×(number of magnetic moment placement positions).

Moreover, according to Patent Literature 1, to obtain the shimming magnetic moment M that satisfies:

$$Ber \approx A \cdot M \quad (2)$$

the following formula, $$M = -A^* \cdot Ber \quad (3)$$

is used to obtain a general inverse matrix $A^*$ using the truncated singular value decomposition (hereinafter, TSVD) method. Accordingly, the shimming magnetic moment M is obtained as, $$M = \Sigma(-v_j \cdot C_j / \lambda_j) \quad (4)$$

Calculation of sum ($\Sigma$) in Formula (4) is performed based on an eigenmode obtained by singular value decomposition (SVD). The eigenmode represents a relationship between a base $v_j$ of the shimming magnetic moment M and a base $u_j$ of the magnetic field distribution Bcom. Each of the eigenmodes has a singular value $\lambda_j$ that represents a magnetic field intensity of a unit magnetic moment (norm: 1) per placement. In addition, eigenmode intensity $C_j$ has a same unit as the magnetic field intensity and is determined by an inner product of eigen magnetic field distribution and the error magnetic field distribution Ber.

In addition (calculation of Σ) of Formula (4), as a reference value for selecting the eigenmode to be a target of the addition, the eigenmode intensity and an order of the eigenmode are used. The order of the eigenmode represents the number indicating the order when the singular value $\lambda_j$ of each of the eigenmodes is arranged in order from the highest value.

In other words, as an eigenmode used in addition (calculation of Σ) in Formula (4), selection is performed such that the eigenmode intensity $C_j$ is sufficiently smaller than the final permissible error magnetic field, and the order of the eigenmode is a predetermined upper limit or less. At this time, a shimming operator has determined the upper limit value of the order of the eigenmode used in addition (calculation of Σ) in Formula (4), namely, the eigenmode as a calculation target of the shimming magnetic moment M (hereinafter, referred to as the upper limit value of the order at the time of addition of the eigenmode) has been determined by appropriately comparing the eigenmode intensity $C_j$ with the permissible intensity of the magnetic field error.

FIGS. 6A and 6B are exemplary graphs, described in Patent Literature 1, displayed on a display device at a time of selecting the eigenmode used in addition of obtaining placement of the shimming magnetic moment. FIG. 6A is a graph before shimming and FIG. 6B is a graph after shimming. The vertical axis of the graph represents logarithm of the eigenmode intensity, and the horizontal axis represents the order of the eigenmode. In the graph, the x-mark 16 in the graph represents one eigenmode, and the circled x-mark 15 represents the eigenmode used for addition in Formula (4). The horizontal line 3 in the graph is a line representing a lower limit value of the eigenmode intensity $C_j$ used in addition. The eigenmodes positioned above this line are candidates for addition. The vertical line 2 represents an upper limit value of the order at the time of addition of the eigenmodes used for the addition (namely, the lower limit value of the singular value $\lambda_j$).

Accordingly, calculation using Formula (4) is performed for the eigenmodes (eigenmodes represented by the circled x-marks 15) determined by the horizontal line 3 (lower limit value of the eigenmode intensity $C_j$) and by the vertical line 2 (lower limit value of the singular value $\lambda_j$). With this calculation, the shimming magnetic moment M is obtained. Subsequently, by using Formula (1), it is possible to calculate the magnetic field distribution Bcom to be corrected by the shimming magnetic moment M.

Conventionally, a residual magnetic field distribution Bres that remains after correction has been estimated by the formula, $$Bres = Ber - Bcom \qquad (5)$$

and based on the magnitude of the amount of variation of the residual magnetic field distribution Bres, validity of the eigenmode determined by the two lines of the horizontal line 3 and the vertical line 2, namely validity of the condition for addition in Formula (4) has been confirmed.

In FIG. 6A, as an index that indicates the magnitude of the amount of variation of the residual magnetic field distribution Bres, a value has been obtained by dividing a difference between the maximum value and the minimum value (hereinafter, referred to as a peak to peak (PP) value) of the element of the residual magnetic field distribution Bres, by an average magnetic field intensity, a target magnetic field intensity, or the like, in a measured magnetic field area. A ppm value (one millionth value) of the obtained value is indicated at an upper portion of the graph as an attainable homogeneity 17.

A shimming operator compares the displayed attainable homogeneity 17 with the predetermined target accuracy. When the attainable homogeneity 17 is larger than the target accuracy, the operator increases the upper limit value of the order at the time of addition of the eigenmode so as to increase the eigenmode to be used in addition in Formula (4). With this operation, the shimming magnetic moment M is readjusted to improve the attainable homogeneity 17.

This type of shimming method can be defined as operation for setting a suitable target magnetic field intensity, the vertical line 2, the horizontal line 3, or the like, by using the graphs in FIGS. 6A and 6B. In this context, the shimming operation might be slightly in a form of trial and error operation. Still, repeating this adjustment operation, it is possible to perform adjustment (shimming) to reliably achieve a good magnetic field distribution as illustrated in FIG. 6B. Note that the attainable homogeneity 17 illustrated in FIG. 6A is an estimation value before shimming, and the attainable homogeneity 17a illustrated in FIG. 6B is a value obtained from the measured magnetic field after shimming.

CITATION LIST

Patent Literature

Patent Literature 1: JP 4902787 B

SUMMARY OF INVENTION

Technical Problem

The present invention is intended to improve points that have been partially in a form of trial and error operation in a conventional shimming method based on Patent Literature 1. By analyzing operation of conventional shimming, it has been found that the operation is configured with four steps as follows.

(1) Measuring a magnetic field distribution.

(2) Calculating an error magnetic field distribution Ber that is a difference between a target magnetic field distribution Btg and a measured magnetic field distribution. When it is determined that the error magnetic field distribution Ber is smaller than a predetermined magnetic field intensity, shimming is finished.

(3) Calculating the shimming magnetic moment M using Formula (4).

(4) According to the calculated shimming magnetic moment M, a piece of hardware constituting a magnetic moment including an iron piece, a magnetic piece, and a current loop is actually placed.

The target magnetic field distribution Btg is a vector having target magnetic field intensity at each of measurement points as its element. In a case of MRI, an identical number is arranged as the element of the target magnetic field distribution Btg.

The shimming operation repeats the operation described in (1) to (4) above until the measured magnetic field distribution reaches target homogeneity. The present invention relates to (3) among these steps. The latter half of step (2) to step (3) can be further divided into more specific steps as follows.

(Latter half of (2)) Displaying the magnetic field intensity of the calculated error magnetic field distribution Ber at each of the measurement positions, onto a display device. If the magnetic field intensity is high, shimming is repeated.

(3-a) Decomposing the error magnetic field distribution Ber into eigenmodes. Calculating singular value $\lambda_j$, and the eigenmode intensity $C_j$ for each of the eigenmodes.

(3-b) Setting an eigenmode selecting condition.

(3-c) Based on the displayed attainable homogeneity 17, determining validity of the selecting condition of the eigenmode.

(3-d) When the attainable homogeneity 17 is determined as not valid, repeating (3-b) to (3-d). When the attainable homogeneity 17 is valid, converting the magnitude of the shimming magnetic moment M at each of the placement positions into the size of an iron piece, a magnetic piece, permanent magnet, current loop, or the like, and displaying the result on the display device.

The selecting condition of the eigenmodes includes the target magnetic field distribution Btg, the lower limit value of the eigenmode intensity $C_j$ (corresponding to the horizontal line 3 in FIGS. 6A and 6B), and the upper limit value of the order at the time of addition of the eigenmode (corresponding to the vertical line 2 in FIGS. 6A and 6B). Among these, the lower limit value of the eigenmode intensity $C_j$ causes no particular problem selection just by setting it to a very little value; however, the other two needs sufficient examination.

According to description of Patent Literature 1, in determination of the upper limit value of the order at the time of addition of the eigenmode, the operator determines the value by watching distribution of the x-marks 16 of the eigenmodes displayed in the graph in FIG. 6A. However, in a stage before eigenmode selecting condition has been determined, the attainable homogeneity 17 is not displayed in the graph in FIG. 6A, although the x-marks indicating the eigenmodes are displayed. The timing of displaying the attainable homogeneity 17 would be after eigenmode selecting condition has been determined, that is, after the target magnetic field distribution Btg, the lower limit value of the eigenmode intensity $C_j$, and the upper limit value of the order at the time of addition of the eigenmode have been determined, and then Formula (4), or the like, has been calculated.

Accordingly, even in a case where the target magnetic field distribution Btg and the lower limit value of the eigenmode intensity $C_j$ have been determined and thereafter, the upper limit value of the order at the time of addition of the eigenmode is to be determined, the operator would have to determine once the upper limit value of the order and watch the display of the attainable homogeneity 17 before being able to determine validity of the determined upper limit value of the order. When the once-determined upper limit value of the order has not been appropriate, it is not easily understandable from the display of the attainable homogeneity 17 how to determine the upper limit value of the order to be determined next. With this context, the operator is required to perform trial and error operation repetitively including determination of the upper limit value of the order at the time of addition of the eigenmode, and determination of whether the determined upper limit value of the order has been valid based on the attainable homogeneity 17 displayed accordingly.

The present invention is directed to a shimming assistance unit, a shimming assistance method, and an MRI apparatus which promptly and appropriately determines an upper limit value of the order at the time of addition of the eigenmode when an operator executes a shimming, thereby achieving efficient shimming operation.

Solution to Problem

The shimming assistance unit according to the present invention includes: a means for calculating an error magnetic field distribution of a difference between a measured magnetic field distribution or a magnetic field distribution calculated based on a temporary placement of a magnetomotive force, and a target magnetic field distribution; a means for calculating a singular value and a magnetic field intensity of each of eigenmodes by performing singular value decomposition of a response matrix that represents a relationship between the error magnetic field distribution and a placement distribution of a shimming magnetic moment that generates a magnetic field for cancelling the error magnetic field distribution; a means for calculating a residual magnetic field distribution of a difference between the magnetic field distribution generated by the magnetic field intensity of an eigenmode that is a target of calculation of the shimming magnetic moment and the error magnetic field distribution by adding a selected eigenmode to a target of calculation of the shimming magnetic moment while selecting the eigenmode one by one in order from the highest singular value from among the eigenmodes; a means for calculating the residual magnetic field error that represents a fluctuation range of the calculated residual magnetic field distribution as a function value of an order of the eigenmode that is a number put to an order of the level of the singular value; and a means for displaying on a display device the calculated residual magnetic field error as a function graph of the order of the eigenmode.

Advantageous Effects of Invention

According to the present invention, it is possible when an operator performs shimming, to promptly and appropriately determine an upper limit value of the order of the eigenmode that is a target for calculation of a shimming magnetic moment, leading to achieving more efficient shimming operation.

BRIEF DESCRIPTION OF DRAWINGS

FIGS. 6A and 6B are exemplary graphs displayed on the display device at selection of the eigenmode used for addition to obtain placement of the shimming magnetic moment described in Patent Literature 1. FIG. 6A is a graph before shimming, and FIG. 6B is a graph after shimming.

DESCRIPTION OF EMBODIMENTS

Figure 1:
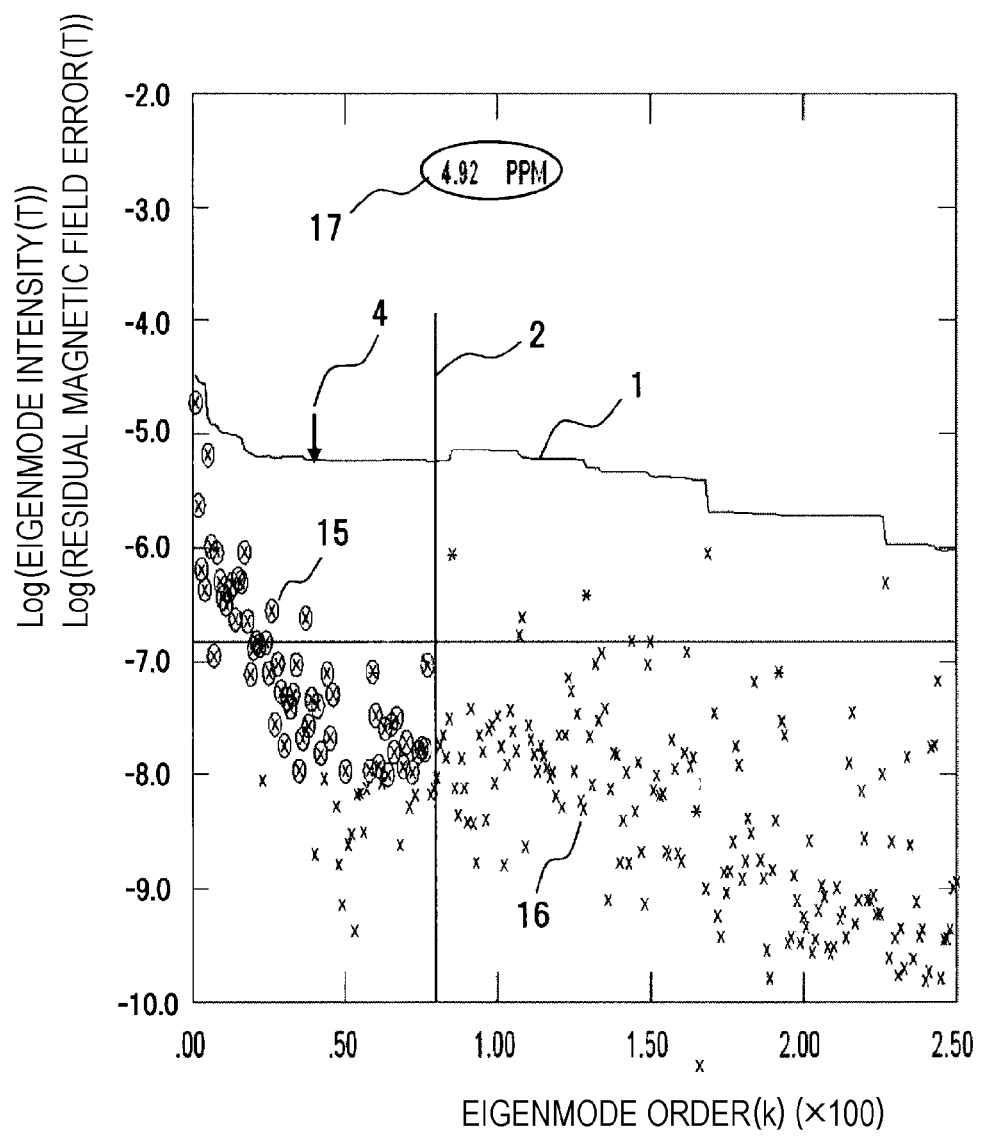
FIG. 1 is an exemplary diagram illustrating a residual magnetic field error Er (k) displayed on a display device as a function of an order k of an eigenmode.

Hereinafter, embodiments of the present invention will be described with reference to the drawings. First, a method for calculating the residual magnetic field distribution Bres will be described.

Fundamental portions of the methods for calculation according to the present embodiment are based on the methods described in Patent Literature 1. Accordingly, description of the above-described TSVD method and of Formulas (1) to (5) will generally be applied to the present embodiment.

In the present embodiment, Formulas (1) to (5) are solved first so as to obtain Formula (6) for calculating the residual magnetic field distribution Bres.

$$Bres = Ber - A \cdot M \quad (6)$$
$$= Ber - A \cdot \{\Sigma(-v_j \cdot C_j / \lambda_j)\}$$

This Formula signifies that performing shimming once would improve the error magnetic field distribution Ber to be the residual magnetic field distribution Bres indicated in Formula (6).

Accordingly, in the present embodiment, the residual magnetic field distribution Bres is treated as a function of N, namely, an upper limit value of the order at the time of addition of the eigenmode in Formula (6). Subsequently, the residual magnetic field distribution Bres when addition (calculation of $\Sigma$) of the eigenmodes in Formula (6) is performed up to the order k (N=k) will be described as a Bres (k).

Moreover, a difference (PP value) between the maximum value and the minimum value of elements of the residual magnetic field distribution Bres (k) is obtained and determined as a residual magnetic field error Er (k).

It is possible determine a root mean square (rms) of the elements of the residual magnetic field distribution Bres (k) as the residual magnetic field error Er (k); however, in the present embodiment, the residual magnetic field error Er (k) is determined to be the difference (PP value) between the maximum value and the minimum value of the elements of the residual magnetic field distribution Bres (k).

Herein, the target magnetic field distribution Btg and the lower limit value of the eigenmode intensity $C_j$ are assumed to be already provided. As described above, the eigenmode intensity $C_j$ may be set to a very small value with no problem.

Conventionally, calculation of the residual magnetic field error Er (k) has been performed such that, for Formula (6) calculation, addition (calculation of $\Sigma$) is performed for the eigenmode with the order up to the upper limit value k, then, the residual magnetic field distribution Bres (k) is obtained, thereafter, the residual magnetic field error Er (k) is obtained.

In the present embodiment, when the residual magnetic field distribution Bres (k−1) for N=k−1 has been obtained, the residual magnetic field distribution Bres (k) for N=k can be calculated by $$Bres(k) = Bres(k-1) - u_k \cdot C_k \quad (7).$$

Herein, $u_k$ represents a base of the magnetic field distribution corresponding to the eigenmode of the order k. An initial value Bres (0) of the residual magnetic field distribution Bres (k) can be obtained, for example, as the amount of difference between the magnetic field intensity calculated at each of magnetic field measurement points before shimming and a target magnetic field intensity.

In other words, by using Formula (7), just by adding a magnetic field component ($-u_k \cdot C_k$) of the eigenmode of the order k to the already-calculated residual magnetic field distribution Bres (k−1) each time the order k is counted up from one, it is possible to calculate the residual magnetic field distribution Bres (k) for the order k.

Formula (7) operates, while selecting eigenmodes one by one in order from the highest singular value $\lambda_j$, so as to add the selected eigenmode to a calculation target of the shimming magnetic moment M in Formula (4), and based on a magnetic field distribution generated by the eigenmode (magnetic field) intensity $C_j$, as a target for calculation of the shimming magnetic moment M, to calculate the residual magnetic field distribution Bres.

With this operation, it is possible, in the present embodiment, to calculate the residual magnetic field distribution Bres (k) quickly in a short time. As a result, it is possible to calculate the residual magnetic field error Er (k) for k=1, 2, 3, . . . quickly in a short time.

As described above, the TSVD method has a significant advantage that it is possible to recognize contribution to the residual magnetic field distribution Bres (k) for each of the eigenmodes. In addition, calculating Formula (7) by selecting the eigenmodes in order from a lowest-order eigenmode in sequence (namely, in order from the eigenmode with highest singular value $\lambda_j$) means utilizing in sequence from the component with in order from the highest magnetic field intensity (singular value $\lambda_j$) per unit magnetic moment. As a result, it is possible to decrease the amount of hardware such as the iron piece and the magnetic piece, that are to be placed in practice as the shimming magnetic moment M.

Meanwhile, for calculation of the residual magnetic field distribution Bres (k), it is possible to use a calculation method other than the TSVD method. The response matrix A in Formula (1) is typically a non-regular matrix. Therefore, acquisition of a general inverse matrix A* by using the TSVD method has been described above. Alternatively, there is a technique to use the Tihonov regularization method.

Although detailed description will be omitted, the Tihonov regularization method can be used to obtain the following from Formula (1).

$$A^T \cdot Ber = (A^T \cdot A + \alpha^2 \cdot L^T \cdot L) \cdot M \quad (8)$$

Herein, $A^T$ is a transposed matrix of the response matrix A. Herein, $\alpha$ represents a regularization parameter. A matrix L is a matrix having a randomness. For the matrix L, an identity matrix In in which all diagonal elements are "1", and all non-diagonal elements are "0" is normally selected.

The identity matrix In is a square matrix of n rows and n columns when the number of components of the shimming magnetic moment M is n. On the other hand, the response matrix A is a matrix of m rows and n columns when the number of components of the error magnetic field distribution Ber is m. Accordingly, $(A^T \cdot A + \alpha^2 \cdot L^T \cdot L)$ in Formula (8) is a regular matrix of n rows and n columns, and an inverse matrix can be obtained.

Therefore, from Formula (8), the following Formula (9) is obtained.

$$M = (A^T \cdot A + \alpha^2 \cdot L^T \cdot L)^{-1} \cdot A^T \cdot Ber \quad (9)$$

Formula (9) signifies that the shimming magnetic moment M is a function of the regularization parameter $\alpha$. According to Formulas (1) and (5), it is possible to obtain the residual magnetic field distribution Bres from the shimming magnetic moment M. Therefore, the residual magnetic field distribution Bres would also be a function of the regularization parameter $\alpha$.

Based on this, it is possible to obtain the following Formula $$Bres(\alpha) = Ber - A \cdot M(\alpha) \quad (10)$$

Furthermore, it is possible to obtain a residual magnetic field error Er (α) from the PP value of the element of the residual magnetic field distribution Bres (α).

The relationship between the regularization parameter α and the singular value $\lambda_j$ will be considered based on Formula (4). In the TSVD method, weights of the eigenmode intensity Cj for selected eigenmodes are all 1.0. In contrast, the weight in case of the Tihonov regularization is $\lambda_j^2/(\lambda_j^2+\alpha^2)$. Accordingly, in the Tihonov regularization, calculation and selection of eigenmode are not executed explicitly; however, addition in Formula (4) is generally executed based on the eigenmode of $\lambda_j^2>\alpha^2$. That is, both provides a substantially equivalent shimming magnetic moment M.

In the present embodiment, the above-described calculation of the residual magnetic field distribution Bres and of the residual magnetic field error Er are executed by the shimming assistance unit that includes a computer. In short, the shimming assistance unit can execute calculation processing of Formulas (1) to (9), obtain the eigenmode by singular value decomposition of the TSVD method, and calculate the residual magnetic field distribution Bres (N) and the residual magnetic field error Er (N) that depend on the upper limit value N of the order of the eigenmode addition at the time of calculation of the shimming magnetic moment M. Similarly, the shimming assistance unit can calculate the residual magnetic field error Er (α) that depends on the regularization parameter α by using the Tihonov regularization.

In many cases, as a calculation model for obtaining the magnetic moment, as stated in Patent Literature 1, the current potential defined in a node of a triangular element is used. It is possible to consider that the current potential on the node is similar to a current value circulating the node. Accordingly, it is also possible to calculate the matrix A using a calculation method in which a magnetic dipole is placed on the node. Accordingly, the calculation method in which the magnetic dipole is placed on the node has no particular difference compared with the calculation method to place the current potential. In this context, even in a case where the magnetic dipole is placed, it is also possible, similarly to the above discussion, to calculate shimming magnetic moment to be placed and homogeneity by using a regularization parameter or function of the order of the eigenmode.

The shimming assistance unit according to the present embodiment includes a display device for displaying a result of calculation processing, such as a liquid crystal display device and a printing device. The shimming assistance unit displays, on the display device, the residual magnetic field error Er (k) or Er (α) obtained as a result of calculation processing, as a graph of function that depends on the order k of the eigenmode or on the regularization parameter α. In this case, the order k represents the upper limit value N of the order at the time of addition of the eigenmode.

Hereinafter, detailed description follows with reference to the drawings. The graph thus displayed representing the residual magnetic field error Er (k) or Er (α) is nothing but a graph that illustrates the attainable homogeneity of the magnetic field distribution Bcom generated in a measured magnetic field area, or attainable homogeneity of the magnetic field distribution generated by placement of a magnetomotive force. By changing the target magnetic field distribution Btg, it is possible to display several similar types of graphs. With these graphs displayed, a shimming operator and a magnetic field designer can easily grasp shimming conditions for achieving a homogeneous magnetic field distribution.

FIG. 1 is an exemplary diagram illustrating a residual magnetic field error Er (k) displayed on a display device as a function of an order k of an eigenmode. In this case, the order k signifies the upper limit value N of the order at the time of addition of the eigenmode. In FIG. 1, the horizontal axis represents the order k of the eigenmode; the vertical axis represents logarithm of the residual magnetic field error. The line graph 1 displayed in FIG. 1 the residual magnetic field error Er (k) obtained as a PP value of the element of the residual magnetic field distribution Bres (k) calculated each time the eigenmode is added in Formula (7).

Moreover, in FIG. 1, the eigenmode intensity in each of the eigenmodes is indicated with x-marks 16 similarly to the case of FIGS. 6A and 6B. When the vertical line 2 specifies the upper limit value N of the order at the time of addition of the eigenmode, the eigenmode intensity $C_j$ used in addition (calculation of Σ) in Formula (4) is indicated with circled x-marks 15. In this case, the vertical axis of the graph in FIG. 1 represents logarithm of the eigenmode intensity.

For example, it is assumed that the target value of the homogeneity of the magnetic field distribution Bcom is 10 µT ($10^{-5}$ teslas) or below, and the line graph 1 is displayed on the display device. At this time, the shimming operator can easily grasp from the line graph 1 that it is possible to achieve the target value of homogeneity at the upper limit value N of the order at the time of addition of the eigenmode at around the arrow 4, that is, the order of the eigenmode is about k=30.

Subsequently, an issue of achieving better magnetic field homogeneity will be discussed. Normally, it is true that the more the upper limit value N (order k) of the order at the time of addition of the eigenmode, the more improved the homogeneity of the magnetic field distribution Bcom. In this case, however, improvement of homogeneity is not always ensured. In other words, the residual magnetic field error Er (k) illustrated in the line graph 1 is not a simple decreasing function of the order k.

In an example in FIG. 1, the residual magnetic field error Er (k) value monotonically decreases up to around the order k of 80. The residual magnetic field error Er (k) value, however, increases around a point where the order k exceeds 80. From this, it is understandable that continuing addition of the eigenmode to increase the order k to exceed 80 would degrade homogeneity of the magnetic field distribution Bcom.

Furthermore, compared with the case there the order k is 30, the case in which the order k is 80 is capable of decreasing the residual magnetic field error Er (k) only with a very small difference. Increasing the order k, namely, increasing the upper limit value N of the order at the time of addition of the eigenmode, means increasing the amount of hardware of the shimming magnetic moment M. Accordingly, in this case, it is necessary to determine the upper limit value N (order k) of the addition of the eigenmode, after sufficiently considering the increase of the amount of hardware.

When the shimming operator has set the upper limit value N of the order at the time of addition of the eigenmode with the vertical line 2, by using FIG. 1, it is possible to calculate the attainable homogeneity 17 as the case in FIGS. 6A and 6B, and to display it together with the displayed line graph 1.

As described above, in the present embodiment, the relationship between the order k of the eigenmode and the residual magnetic field error Er (k) representing homogeneity of the magnetic field distribution Bcom is displayed in the line graph 1. Therefore, it is possible for the shimming operator to quickly and appropriately determine the upper limit value N of the order at the time of addition of the eigenmode. In other words, it is possible to quickly and appropriately determine validity of the upper limit value N of the order at the time of addition of the eigenmode.

Figure 2:
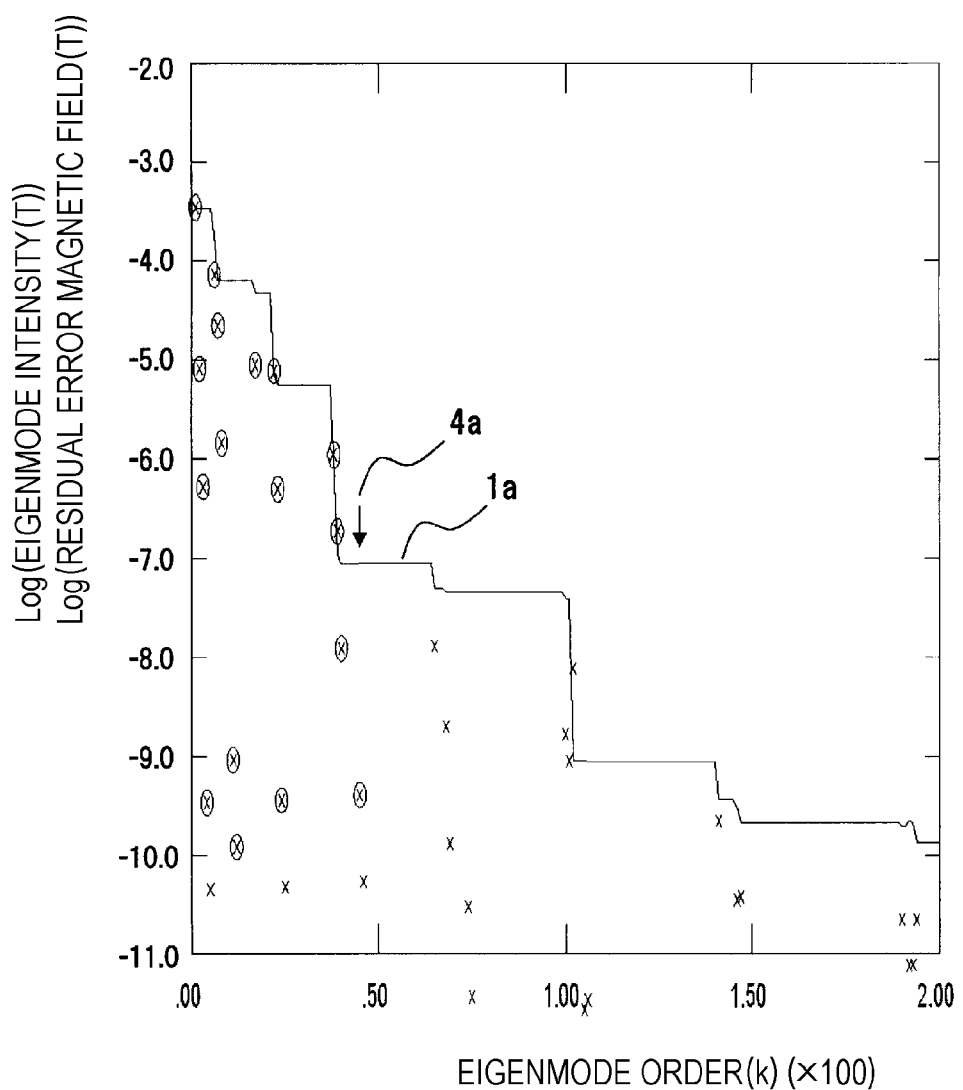
FIG. 2 is another exemplary diagram of the residual magnetic field error Er (k) displayed on the display device as the function of the order k of the eigenmode.

FIG. 2 is another exemplary diagram illustrating the residual magnetic field error Er (k) displayed on the display device as a function of the order k of the eigenmode. In many cases, as described above, when the upper limit value N of the order at the time of addition of the eigenmode, namely, the order k is increased, the residual magnetic field error Er (k) representing homogeneity of the magnetic field distribution Bcom is decreased, leading to improvement of homogeneity of the magnetic field.

As illustrated as the line graph 1a in FIG. 2, homogeneity of the residual magnetic field error Er (k), namely, homogeneity of the magnetic field distribution Bcom, often improves significantly when a specific eigenmode is added. In an example in FIG. 2, at a position where the eigenmode has been added around the order of k=45 indicated with the arrow 4a, homogeneity of the magnetic field distribution Bcom has improved significantly (the residual magnetic field error Er (k) has decreased).

In this case, accordingly, it is understandable that, as the upper limit value N of the order at the time of addition of the eigenmode, it is desirable to select the order k immediately after the residual magnetic field error Er (k) has been significantly reduced. Accordingly, with a configuration in which the graph indicating the residual magnetic field error Er (k) is displayed on the display device, in the present embodiment, it is possible for the shimming operator to quickly and appropriately grasp the upper limit value N of the order at the time of addition of the eigenmode and to determine its validity quickly and appropriately.

Note that in FIGS. 1 and 2, Er (k) is displayed with the function of the order k of the eigenmode in the TSVD method as the line graphs 1 and 1a indicating the attainable homogeneity of the magnetic field distribution Bcom. Alternatively, when the Tihonov regularization is used, Er ($\alpha$) is displayed with a function of the regularization parameter $\alpha$.

Conversion from the shimming magnetic moment M obtained in Formula (4) into the physical amount (the amount of hardware) including the amount of iron piece, magnet, or current loop, can be executed using a similar method described in Patent Literature 1, or the like, although description is omitted in the present description.

Meanwhile, in determination of whether shimming has been generally good, it is necessary to examine not only attainable homogeneity of the magnetic field but also the physical amount such as the amount of iron piece required for shimming. In a case where excessive physical amount is required, selection of the eigenmode, or the like, will be reexamined. In a case where the calculation result is that the excessive physical amount would be required regardless of types of selection, it is determined that there is a failure in magnet design or production.

As illustrated in FIGS. 1 and 2 as above, the function of displaying the residual magnetic field error Er on the display device as the order k of the eigenmode or the function of the regularization parameter $\alpha$ can be utilized in (a) quality control at completion of production (b) determination of validity of design of magnetomotive force placement, and determination of necessity of reexamination of placement, at the time of designing the coil and the magnetic body placement.

In a case where application to magnet design is performed, magnetomotive force placement (placement of the coil and the magnetic body) is temporarily determined, and the magnetic field generated by the placement is calculated so as to obtain placement of a required magnetic moment. This type of placement can also be categorized as shimming in calculation. Accordingly, it is possible use a similar calculation method as described in the present embodiment. In a case where homogeneity of the residual magnetic field distribution Bres is not satisfactory, or the physical amount of required magnetic moment is increased, it is configured to change placement of the magnetic moment such as the coil and iron, so as to minimize the magnetic moment required for shimming.

Figure 3:
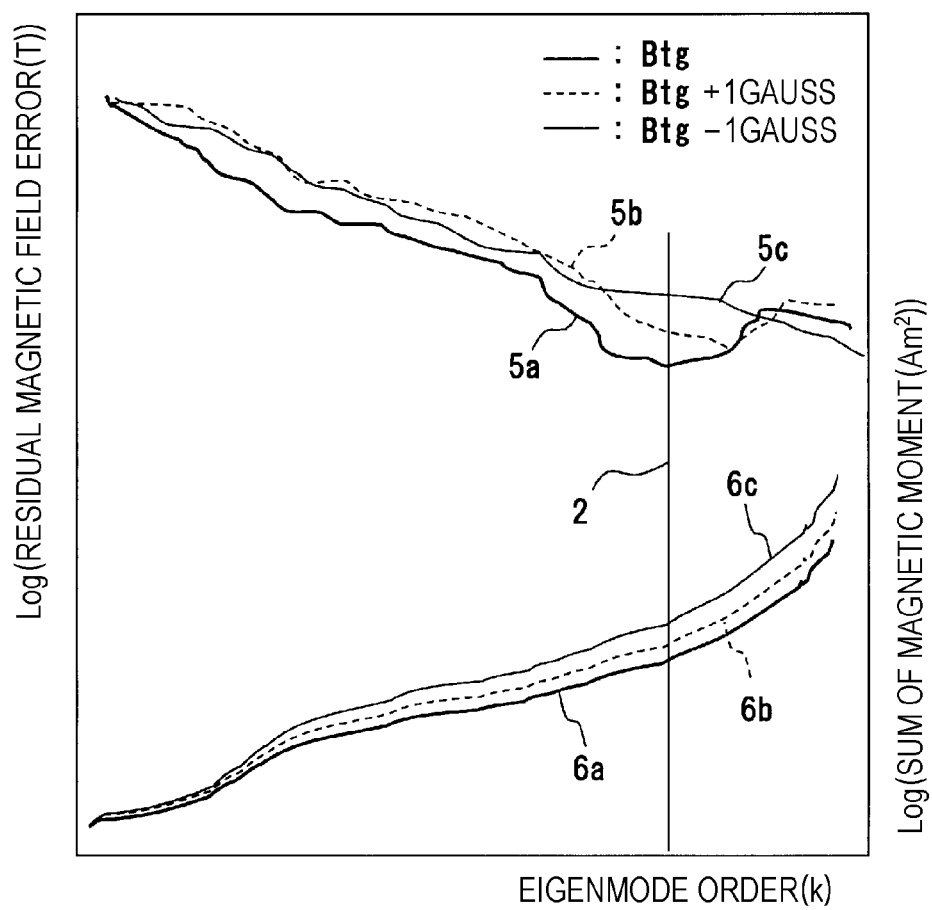
FIG. 3 is an exemplary diagram of a change of a residual magnetic field error Er (k) displayed on the display device when the target magnetic field distribution Btg has been changed.

FIG. 3 is an exemplary diagram of a change in the residual magnetic field error Er (k) displayed on the display device when the target magnetic field distribution Btg has been changed. The horizontal axis represents, similar to the case in FIG. 1, the order k of the eigenmode; the vertical axis represents logarithm of the residual magnetic field error.

Each of the line graphs 5a, 5b, and 5c illustrated in FIG. 3 represents the residual magnetic field error Er (k) as a function graph of the order k. Among these, the line graphs 5b and 5c are graphs that represent the residual magnetic field errors Er (k) when the target magnetic field has been changed from the initial target magnetic field distribution Btg by +1 gauss or −1 gauss, respectively. Note that the intensity of the initial target magnetic field distribution Btg is assumed to be on several tesla (T) order, based on 1 gauss=$10^{-4}$ T.

It is easily understandable from the line graph 5a displayed in FIG. 3 that the residual magnetic field error Er (k) is minimum with respect to the target magnetic field distribution Btg at a position of the vertical line 2. Accordingly, it is easily understandable that setting the order k that corresponds to the position of the vertical line 2 as the upper limit value N of the order at the time of addition of the eigenmode would enable obtaining the best possible homogeneity of the residual magnetic field distribution Bres. Furthermore, by comparing the line graph 5a with the line graphs 5b and 5c, it is easily understandable that improvement in the residual magnetic field error Er (k) would not be expected even when the target magnetic field distribution Btg was changed by +1 gauss or −1 gauss.

Therefore, as illustrated in FIG. 3, with the display of the line graphs 5a, 5b, and 5c indicating the residual magnetic field errors Er (k) when the target magnetic field distribution Btg is slightly changed, the shimming operator will be able to easily recognize the upper limit value N of the order at the time of addition of the eigenmode, and to determine whether the validity preset for the target magnetic field distribution Btg is true.

Moreover, it is configured to calculate a sum total of elements of the shimming magnetic moment M to be a sum total value of magnetic moment, as an approximate standard of the physical amount of the shimming magnetic moment M required at the time of shimming. In FIG. 3, logarithm of the above values is illustrated as the line graphs 6a, 6b, and 6c. With this indication of the amount corresponding to the physical amount of the shimming magnetic moment M in the line graphs 6a, 6b, and 6c, it is possible for the shimming operator to appropriately determine validity of the physical amount of the shimming magnetic moment M.

The horizontal axis in the graph represents the order k of the eigenmode in FIG. 3, but may be a regularization parameter α in the Tihonov regularization.

Figure 4:
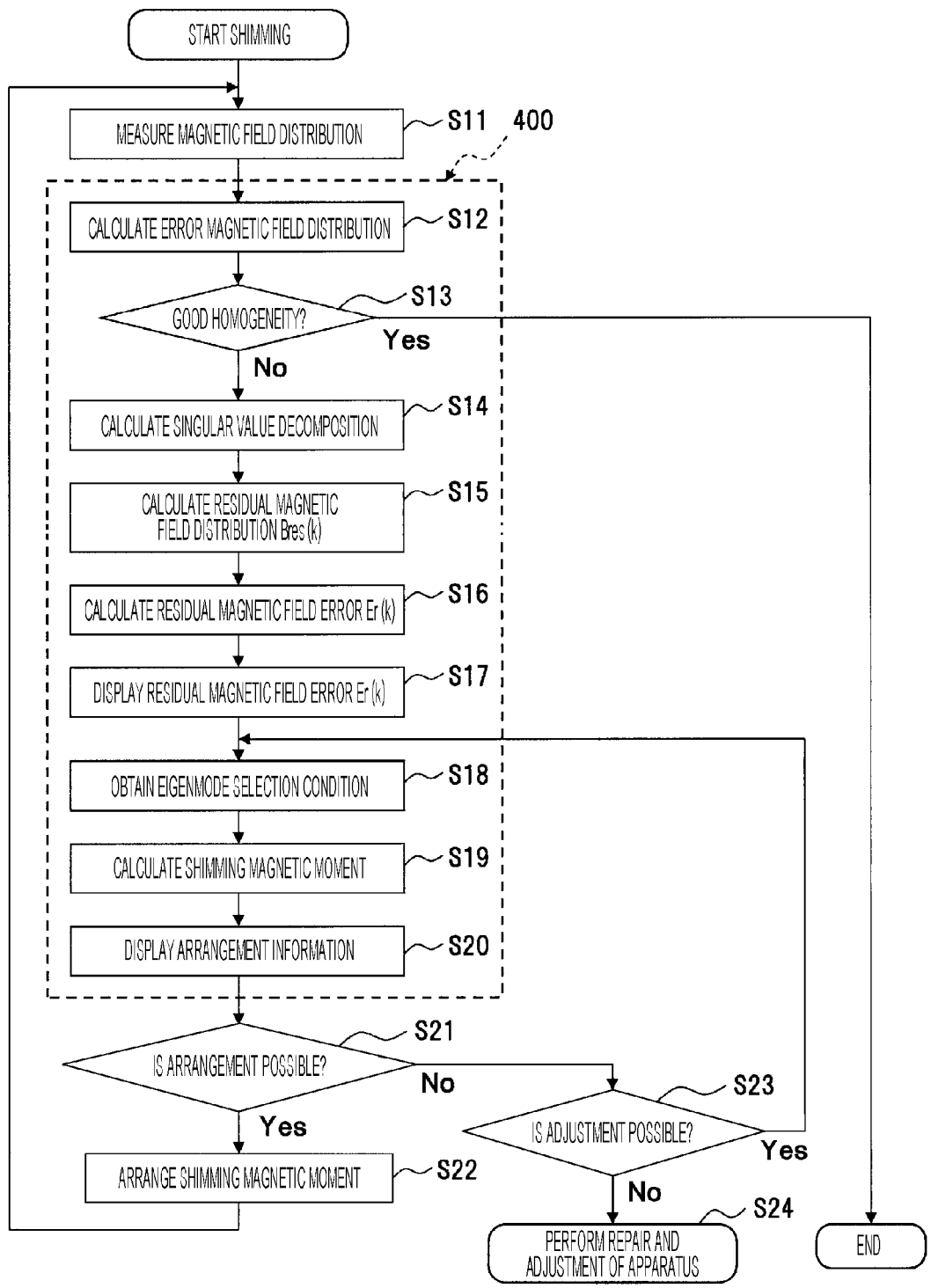
FIG. 4 is an exemplary flow diagram of overall processing of shimming operation when a shimming assistance unit is applied to the shimming operation.

FIG. 4 is an exemplary flow diagram of overall processing of shimming operation when the shimming assistance unit is applied to the shimming operation. In FIG. 4, processing enclosed by dotted lines is executed by the shimming assistance unit.

As illustrated in FIG. 4, a shimming operator starts shimming of a magnet apparatus with measurement of magnetic field distribution generated in a measured magnetic field area by the magnet apparatus by using a magnetic field measurement device (step S11). Next, the shimming assistance unit obtains measured magnetic field distribution from the magnetic field measurement device, and calculates an error magnetic field distribution Ber, namely the difference between the measured magnetic field distribution and the predetermined target magnetic field (step S12). The error magnetic field distribution Ber is a vector having the same number of elements (components) as the number of magnetic field measurement points.

Next, the shimming assistance unit obtains, for example, a difference (PP value) between the maximum value and the minimum value of each of the elements of the error magnetic field distribution Ber, as an index for a fluctuation range of the error magnetic field distribution Ber. Using the PP value, homogeneity of the error magnetic field distribution Ber is determined (step S13). In a case where the PP value is smaller than a predetermined PP value, it means that the generated magnetic field distribution is substantially the same as the target magnetic field distribution. Accordingly, homogeneity of the generated magnetic field is determined to be good (Yes in step S13), and then, the shimming operation is finished. On the other hand, in a case where the PP value is the predetermined PP value or more, homogeneity of the generated magnetic field is determined to be a failure (No in step S13), and processing moves step S14 and later processing.

The shimming assistance unit obtains the response matrix A that satisfies Formula (2), and performs singular value decomposition calculation so as to obtain a general inverse matrix A* of the response matrix A (step S14). This singular value decomposition calculation may be pre-calculated before starting the operation so as to reduce operation time. As a result of the singular value decomposition, a singular value $\lambda_j$ for each of the eigenmodes and the eigenmode (magnetic field) intensity Cj are obtained.

Next, the shimming assistance unit calculates the residual magnetic field distribution Bres (k) according to Formulas (4) and (5) using the singular value λj and the eigenmode intensity Cj, while the order k is counted up one by one beginning from one (step S15). The order k herein represents the upper limit value N of the order of the eigenmode to be used for addition (calculation of Σ) in Formula (4). In the present embodiment, the residual magnetic field distribution Bres (k) is calculated by using Formula (7).

Next, the shimming assistance unit calculates the PP value of the elements of the residual magnetic field distribution Bres (k) to be a residual magnetic field error Er (k) (step S16). The residual magnetic field error Er (k) is an index of the fluctuation range of the residual magnetic field distribution Ber, and herein is calculated as a value that depends on the order k of the eigenmode.

Next, the shimming assistance unit displays, on the display device, a graph indicating the residual magnetic field error Er (k) that depends on the order k of the eigenmode (step S17). Display examples of the residual magnetic field error Er (k) are illustrated as the line graphs 1 and 1a in FIGS. 1 and 2.

Next, after watching the graph indicating the residual magnetic field error Er (k) displayed on the display device, the operator inputs a selection condition of the eigenmode that the operator has determined as appropriate (the order of the eigenmode according to the present embodiment). The shimming assistance unit obtains the selection condition of the eigenmode to be input (step S18). Next, the shimming assistance unit calculates the shimming magnetic moment M using Formula (4) according to the selection condition of the obtained eigenmode, namely, the order of the eigenmode (step S19).

Next, the shimming assistance unit displays information on the calculated shimming magnetic moment M, specifically about the size and placement positions of the iron piece, magnetic body, and the current loop to be placed, namely, placement information on each of the magnetic moments, on the display device (step S20).

Then, based on the placement information on each of the magnetic moments displayed on the display device, the shimming operator determines whether the shimming magnetic moment M can practically be placed. In a case where the shimming magnetic moment M can practically be placed (Yes in step S21), the shimming operator practically places each of the magnetic moments including an iron piece for adjustment, a magnetic body, and a current loop (step S22).

Returning to step S11, the operator re-measures magnetic field distribution generated by the magnet apparatus after shimming magnetic moment placement (step S11). Subsequently, the shimming assistance unit calculates the error magnetic field distribution Ber (step S12). In a case where the fluctuation range (PP value) of the error magnetic field distribution Ber is smaller than the predetermined PP value, that is, homogeneity of the generated magnetic field distribution is good (Yes in step S13), shimming is finished.

On the other hand, in a case where it is determined in step S21 that the displayed shimming magnetic moment is too large to be placed in practice (No in step S21), the shimming operator determines whether it is possible to perform adjustment by changing eigenmode selection conditions, or the like (step S23). When this adjustment is determined to be possible (Yes in step S23), the processing returns to step S18, and then, processing of step S18 and the subsequent steps are executed repetitively by the shimming assistance unit.

On the other hand, when the adjustment by changing selection condition, or the like, is determined to be impossible in step S23 (No in step S23), it is determined that there is a failure in the magnet apparatus, and the magnet apparatus is repaired and adjusted (step S24).

According to the above-described shimming operation, the operator will be able to input the selection condition of the eigenmode while watching the line graphs 1 and 1a (refer to FIGS. 1 and 2) indicating the residual magnetic field error Er (k) displayed in step S17. With this configuration, it is possible for the operator to quickly and appropriately select the eigenmode that is suitable for improving homogeneity of the magnetic field distribution. As a result, it is possible for the operator to improve homogeneity of the magnetic field distribution without repetitively selecting the eigenmode in shimming, leading to reduced time required for the shimming operation.

Figure 5:
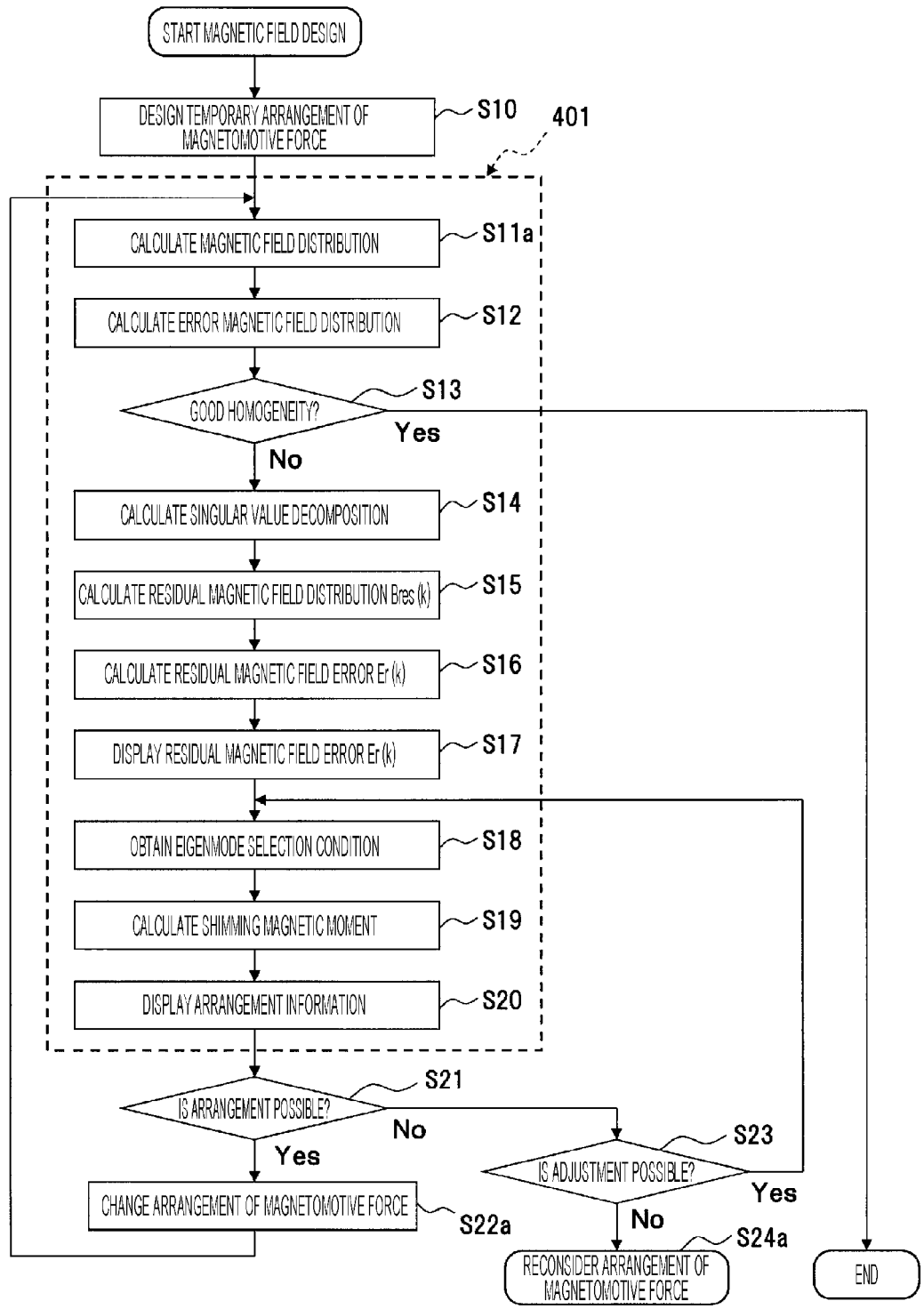
FIG. 5 is an exemplary flow diagram of overall processing of magnetic field design operation when the shimming assistance unit is applied to the magnetic field design operation.

FIG. 5 is an exemplary flow diagram of overall processing of magnetic field design operation when the shimming assistance unit is applied to the magnetic field design operation. In FIG. 5, processing enclosed by dotted lines is executed by the shimming assistance unit.

As illustrated in FIG. 5, a magnetic field designer starts designing of the magnetic field using a magnet apparatus with designing temporary placement of a magnetomotive force using the magnet apparatus (step S10). Next, the shimming assistance unit calculates the magnetic field distribution generated at a predetermined measured magnetic field area by the magnet apparatus, based on the temporary placement of the magnetomotive force (step S11a). Next, the shimming assistance unit calculates an error magnetic field distribution Ber, namely the difference between the calculated magnetic field distribution and the predetermined target magnetic field (step S12).

Next, the shimming assistance unit obtains, for example, a difference (PP value) between the maximum value and the minimum value of each of the elements of the error magnetic field distribution Ber, as an index for a fluctuation range of the error magnetic field distribution Ber. Using the PP value, homogeneity of the error magnetic field distribution Ber is determined (step S13). In a case where the PP value is smaller than a predetermined PP value, it means that the magnetic field distribution generated by the magnet apparatus is substantially the same as the target magnetic field distribution. Accordingly, homogeneity of the generated magnetic field is determined to be good (Yes in step S13). Accordingly, the temporary placement of the magnetomotive force at that time is determined as the finally designed magnetomotive force placement, and the magnetic field design operation is finished.

On the other hand, in a case where the PP value is the predetermined PP value or more, homogeneity of the generated magnetic field is determined to be failure (No in step S13), and processing moves to processing of step S14 and the subsequent steps. For processing from step S14 to step S20 are the same as the processing of the shimming assistance unit illustrated in FIG. 4, thus, description will be omitted. The singular value decomposition calculation in step S14 may be calculated beforehand. Alternatively, it may be calculated at any time using the temporary placement information, as long as it is on and after temporary placement design of the magnetomotive force in step S10.

Then, based on the placement information on each of the magnetic moments displayed on the display device, the shimming designer determines whether the shimming magnetic moment M can practically be placed. In a case where the shimming magnetic moment M can practically be placed (Yes in step S21), the shimming designer changes the initial temporary placement of the magnetomotive force (step S22a). The shimming assistance unit returns the processing to step S11a and re-calculates magnetic field distribution based on the changed magnetomotive force placement (step S11a).

On the other hand, in a case where it is determined in step S21 that the displayed shimming magnetic moment is too large to be placed practically (No in step S21), the magnetic field designer determines whether it is possible to perform adjustment by changing eigenmode selection conditions, or the like (step S23). When the result indicates that this adjustment is determined to be possible (Yes in step S23), the processing returns to step S18, and then, processing of step S18 and the subsequent steps are executed repetitively by the shimming assistance unit.

On the other hand, when the adjustment by changing selection condition of the eigenmode, or the like, is determined to be impossible in step S23 (No in step S23), it is determined that there is a design flaw in temporary placement of the magnetomotive force, and the temporary placement of the magnetomotive force is reexamined (step S24a).

According to the above-described magnetic field design operation, the magnetic field designer will be able to input the selection condition of the eigenmode while watching the line graphs 1 and 1a (refer to FIGS. 1 and 2) indicating the residual magnetic field error Er (k) displayed in step S17. With this configuration, it is possible for the magnetic field designer to quickly and appropriately select the eigenmode that is suitable for improving homogeneity of the magnetic field distribution. As a result, it is possible for the magnetic field designer to improve homogeneity of the magnetic field distribution without repetitively selecting the eigenmode in the shimming, leading to time reduction in the magnetic field design operation.

Meanwhile, processing executed by the shimming assistance unit described in FIGS. 4 and 5 may be incorporated in a control device of the magnet apparatus equipped with a computer, or the like, or in a control device of an MRI apparatus. This configuration improves efficiency of shimming operation and magnetic field design operation on the magnet apparatus and the MRI apparatus.

As described above, the present embodiment may be applied to a magnet apparatus in which magnetic bodies such as coils and iron pieces are placed for generating high-accuracy magnetic field, including the MRI apparatus for medical diagnosis, and an apparatus for physics research, for a purpose of adjusting or designing the magnetic field to achieve a desirable magnetic field intensity distribution.

The present embodiment is particularly suitable for adjustment or designing of the magnetic field with extremely highly accurate homogeneity, generated in a measured magnetic field area, such as in the MRI apparatus The adjustment operation corrects an error magnetic field by placing the magnetic moments such as iron pieces so as to homogenize the magnetic field intensity. This adjustment operation is referred to as shimming. The shimming assistance unit according to the present embodiment effectively assists the operator in shimming operation with executing determination of conditions for magnetic moment placement calculation.

The present invention is not limited to the above-described embodiment, but may include various types of modification. For example, the above-described embodiment gives detailed explanation just to allow the present invention to be clearly understood. Therefore, the present invention is not limited to the case having all of components in the configuration. A part of configuration of an embodiment can be replaced with a part of configuration of another embodiment. A part or all of the configuration of another embodiment can be added to a certain embodiment.

REFERENCE SIGNS LIST 1, 1a line graph (residual magnetic field error)
2 vertical line (lower limit value of singular value $\lambda_j$)
3 horizontal line (lower limit value of the eigenmode intensity $C_j$)
5a, 5b, 5c line graph (residual magnetic field error)
6a, 6b, 6c line graph (sum total of magnetic moment)
17, 17a attainable homogeneity
$\lambda_j$ singular value of eigenmode j
$C_j$ intensity of eigenmode j (eigenmode intensity)
A response matrix
A* general inverse matrix of response matrix A
$A^T$ transposed matrix of response matrix A
Ber error magnetic field distribution Bres residual magnetic field distribution
Btg target magnetic field distribution
Er residual magnetic field error
K order of eigenmode
M shimming magnetic moment
N upper limit of eigenmode addition

The invention claimed is:

1. A shimming assistance unit comprising:

a means for calculating an error magnetic field distribution of a difference between a measured magnetic field distribution or a magnetic field distribution calculated based on a temporary placement of a magnetomotive force, and a target magnetic field distribution;

a means for calculating a singular value and a magnetic field intensity of each of eigenmodes by performing singular value decomposition of a response matrix that represents a relationship between the error magnetic field distribution and a placement distribution of a shimming magnetic moment that generates a magnetic field for cancelling the error magnetic field distribution;

a means for calculating a residual magnetic field distribution of a difference between the magnetic field distribution generated by the magnetic field intensity of an eigenmode that is a target of calculation of the shimming magnetic moment and the error magnetic field distribution by adding a selected eigenmode to the target of calculation of the shimming magnetic moment while selecting an eigenmode one by one in order from the highest singular value from among the eigenmodes;

a means for calculating the residual magnetic field error that represents a fluctuation range of the calculated residual magnetic field distribution as a function value of an order of the eigenmode that is a number put to an order of level of the singular value; and a means for displaying on a display device the calculated residual magnetic field error as a function graph of the order of the eigenmode.

2. The shimming assistance unit according to claim 1 further comprising:

a means for calculating a sum total of the shimming magnetic moment placed corresponding to the eigenmode for the target of calculation of the shimming magnetic moment, as an index representing a physical amount of the shimming magnetic moment to be placed, and for displaying on a display device the calculated index as a function graph of the order of the eigenmode.

3. A shimming assistance method having a computer execute:

calculating an error magnetic field distribution of a difference between a measured magnetic field distribution or a magnetic field distribution calculated based on a temporary placement of a magnetomotive force, and a target magnetic field distribution;

calculating a singular value and a magnetic field intensity of each of eigenmodes by performing singular value decomposition of a response matrix that represents a relationship between the error magnetic field distribution and a placement distribution of a shimming magnetic moment that generates a magnetic field for cancelling the error magnetic field distribution;

calculating a residual magnetic field distribution of a difference between the magnetic field distribution generated by the magnetic field intensity of an eigenmode that is a target of calculation of the shimming magnetic moment and the error magnetic field distribution by adding a selected eigenmode to the target of calculation of the shimming magnetic moment while selecting an eigenmode one by one in order from the highest singular value from among the eigenmodes;

calculating the residual magnetic field error that represents a fluctuation range of the calculated residual magnetic field distribution as a function value of an order of the eigenmode that is a number put to an order of level of the singular value; and displaying on a display device the calculated residual magnetic field error as a function graph of the order of the eigenmode.

4. The shimming assistance method according to claim 3, the method having the computer further execute:

calculating a total sum of the shimming magnetic moment placed corresponding to the eigenmode that has become the target of calculation of the shimming magnetic moment, as an index representing the physical amount of the shimming magnetic moment to be placed, and displaying on a display device the calculated index as a function graph of the order of the eigenmode.

5. An MRI apparatus comprising the shimming assistance unit according to claim 1.

6. A magnet apparatus comprising the shimming assistance unit according to claim 1.

7. An MRI apparatus comprising the shimming assistance unit according to claim 2.

8. A magnet apparatus comprising the shimming assistance unit according to claim 2.

* * * * *